US00RE33864E

United States Patent [19]

Steiner et al.

[11] E Patent Number: Re. 33,864

[45] Reissued Date of Patent: Mar. 31, 1992

[54] SELF-CONTAINED AIR FRESHENER AND CARTRIDGE THEREFOR

[75] Inventors: Robert L. Steiner, Chicago; Thomas R. Bajek, Downers Grove, both of Ill.

[73] Assignee: Steiner Company, Inc., Chicago, Ill.

[21] Appl. No.: 521,346

[22] Filed: May 9, 1990

Related U.S. Patent Documents

Reissue of:

[64] Patent No.: 4,743,406
Issued: May 10, 1988
Appl. No.: 3,193
Filed: Jan. 15, 1987

[51] Int. Cl.[5] ..... B01F 3/04

[52] U.S. Cl. ..... 261/30; 239/57; 239/59; 239/60; 422/49; 422/124

[58] Field of Search ..... 261/30, DIG. 65; 422/49, 124; 239/57, 59, 60

[56] References Cited

U.S. PATENT DOCUMENTS

| | | | |
|---|---|---|---|
| 2,765,194 | 10/1956 | Will | 239/60 |
| 2,794,676 | 6/1957 | D'Agostino | 239/60 |
| 3,125,407 | 3/1964 | Kagan | 239/57 |
| 3,521,816 | 7/1970 | Wilson | 239/60 |
| 3,527,405 | 9/1970 | Harding | 261/DIG. 65 |
| 3,923,934 | 12/1975 | Watkins | 239/59 |
| 3,990,848 | 11/1976 | Corris | 422/49 |
| 3,993,444 | 11/1976 | Brown | 261/DIG. 65 |
| 4,035,451 | 7/1977 | Tringali | 422/4 |
| 4,040,568 | 8/1977 | Mason, Jr. et al. | 239/57 |
| 4,059,422 | 11/1977 | Steiner | 422/124 |
| 4,111,655 | 9/1978 | Quincey | 422/124 |
| 4,272,261 | 6/1981 | Lynch, Jr. et al. | 261/DIG. 65 |
| 4,301,095 | 11/1981 | Mettler et al. | 422/124 |
| 4,377,399 | 3/1983 | Bryson | 261/DIG. 65 |
| 4,396,557 | 8/1983 | DeLuca | 261/DIG. 65 |

FOREIGN PATENT DOCUMENTS

| | | | |
|---|---|---|---|
| 2257134 | 5/1973 | Fed. Rep. of Germany | 422/124 |

*Primary Examiner*—Tim Miles
*Attorney, Agent, or Firm*—Emrich & Dithmar

[57] ABSTRACT

A self-contained battery-powered room deodorizer including a housing having an inlet portion through which ambient air is drawn into the housing by means of a battery powered fan. The air is passed about a quantity of vaporizable material contained within the housing, and then discharged therefrom into the ambient air carrying the vaporized portion of the product therewith. A replaceable deodorizing material containing cartridge is positionable within the housing, and provides a support well for supporting a replaceable battery, such that the deodorizing material and battery may be separately replaced when either of these items has become expended.

38 Claims, 2 Drawing Sheets

FIG. 1
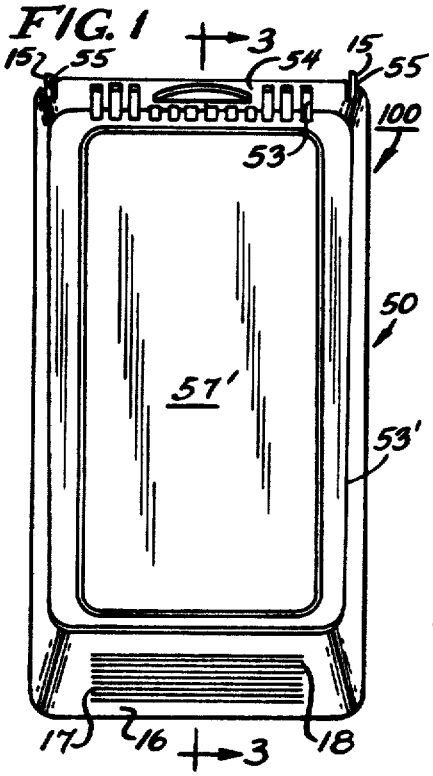
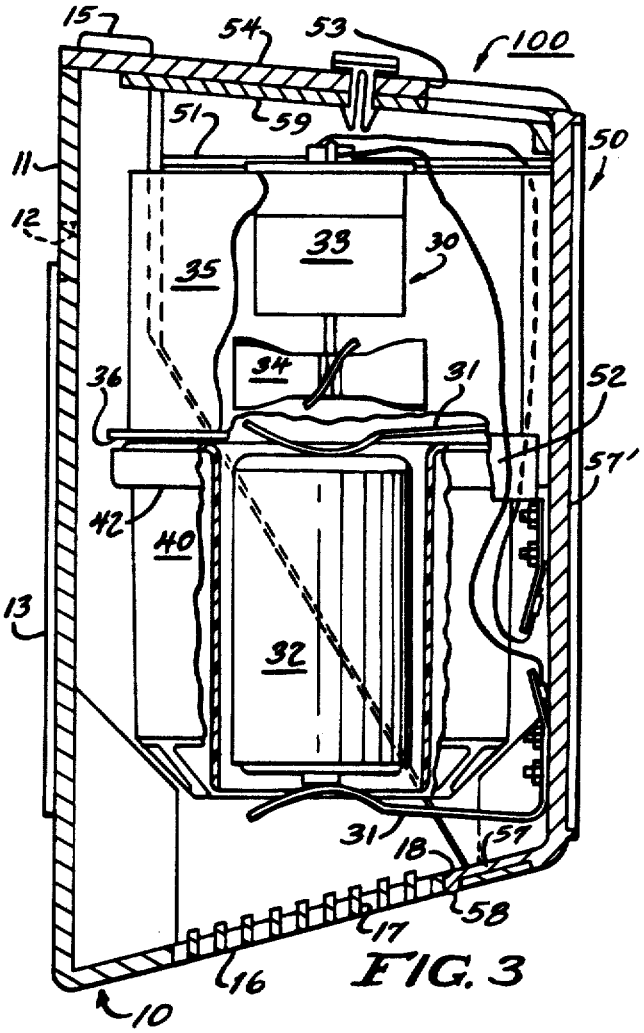
FIG. 3
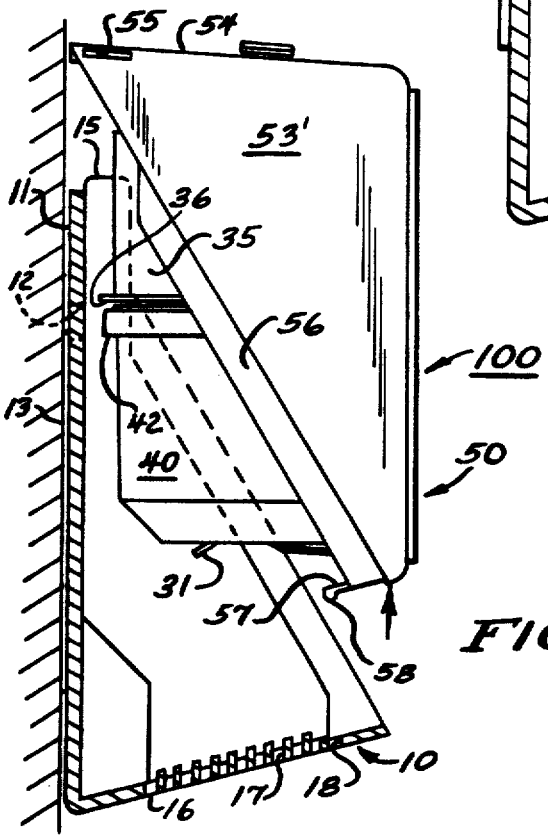
FIG. 2

FIG. 4
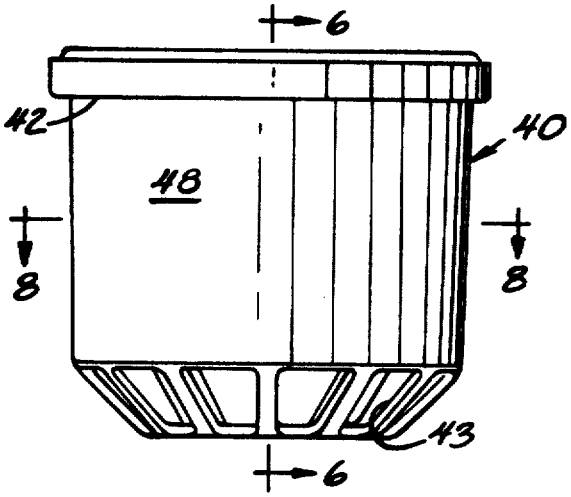
FIG. 5
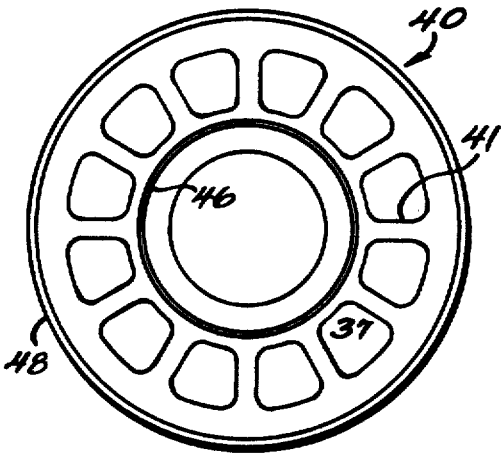
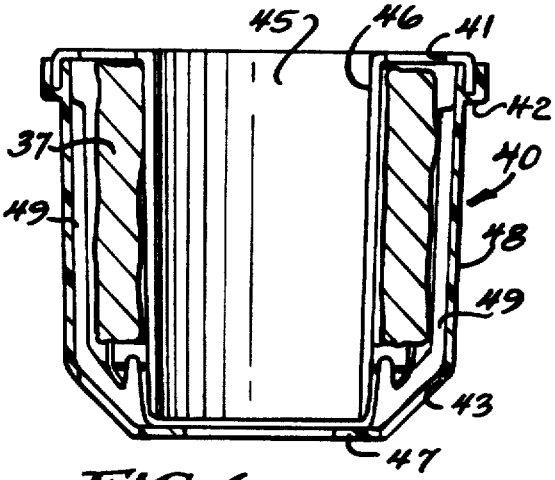
FIG. 6
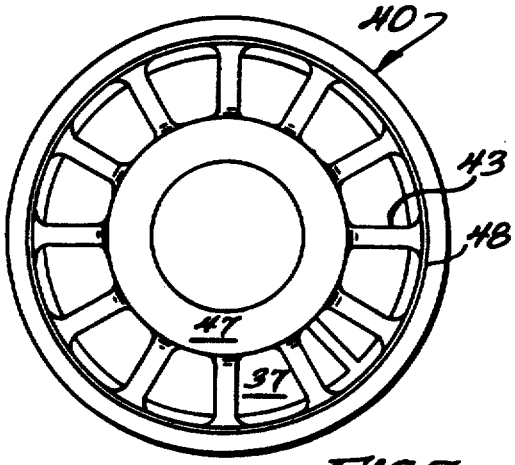
FIG. 7
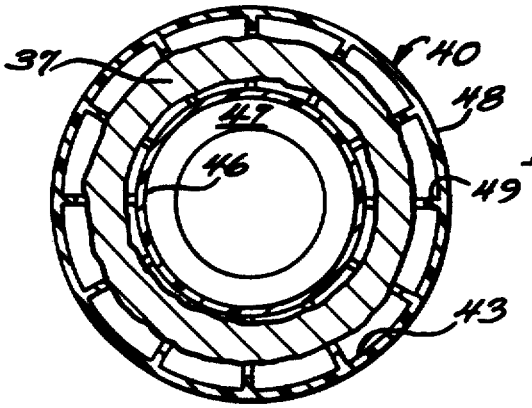
FIG. 8

SELF-CONTAINED AIR FRESHENER AND CARTRIDGE THEREFOR

Matter enclosed in heavy brackets [ ] appears in the original patent but forms no part of this reissue specification; matter printed in italics indicates the additions made by reissue.

*This application is a Reissue of application Ser. No. 07/003,193, filed Jan. 15, 1987, now U.S. Pat. No. 4,743,406.*

BACKGROUND OF THE INVENTION

This invention relates in general to air freshening devices and, in particular, to a self-contained air freshener which draws ambient air through the apparatus, and about or through a deodorizing cartridge to vaporize materials contained in the cartridge for distribution into the air flow.

More specifically, but without restriction to the particular embodiment and/or use which is shown and described for purposes of illustration, this invention relates to self-contained air freshener utilizing a replaceable cartridge containing or formed from a vaporizable material, and a replaceable battery power source. These replaceable or expendable items are carried within the apparatus to permit the convenient and selective replacement of these items when necessary.

Various types of air freshening or deodorizing devices have been utilized for inducing air flow past a product which may be vaporized, either by evaporation or sublimation, in order to distribute the vaporized product throughout the surrounding environment. To this end, apparatus such as disclosed in U.S. Pat. Nos. 3,990,848 and 4,035,451 have been developed to distribute the vaporized product into the environment.

In U.S. Pat. No. 3,990,848, an apparatus is disclosed which utilizes a self-contained disposable cartridge comprising a quantity of vaporizable product contained within a porous container upon which a battery power source is mounted and attached. In this manner, the entire unitary cartridge, product and power source, may be readily replaced with a new cartridge providing both a fresh power supply and a fresh quantity of deodorizer.

In the apparatus disclosed in U.S. Pat. No. 4,035,451 a disposable cartridge, including both a quantity of material capable of being vaporized and a battery power source, is provided with the battery forming an integral part of the support structure for the cartridge. A strip material is folded in a convoluted configuration and concentrically spaced about the battery to define a series of parallel air passageways by which a product impregnated in the strip material is vaporized and distributed into the environment.

While each of these above-identified apparatus functions to distribute the vaporized product into the air, it has been found that the useful life of the vaporizable material and the useful life of the battery power source, are not necessarily the same. Therefore, when both the vaporizable material and the power source are integrated into the same unitary disposable and replaceable cartridge, the useful life of both is determined by the shortest useful life of either. This causes the operational life of cartridge, as a whole, to be shorter than necessary.

In addition these devices, as well as other such devices, are not conveniently serviceable after installation. Preferably such air fresheners are installed in isolated locations where a suitable air flow may be established, with the unit being installed above the un-aided reach of a person to prevent vandalism. Such installations, however, have heretofore necessitated that the units be serviced while the service personnel are standing on a ladder or platform reaching into and working on the unit. Frequently such servicing is done by the service personnel working on the unit, above eye level, requiring servicing to be effected by feel.

The present invention is constructed such that all of the serviceable components of the unit are detachably mounted in a portion of the housing which is separable from the unit. In this manner, after the unit is installed the service personnel can easily remove this portion of the unit in order to effect any required servicing without having to do the servicing while standing on a ladder or by feel.

SUMMARY OF THE INVENTION

It is, therefore, an object of this invention to improve self-contained air freshening or deodorizing devices.

Another object of this invention is to utilize a separate expendable and replaceable deodorizing product and a power source so that either may be replaced as required.

A further object of this invention is to support a replaceable battery within a replacement cartridge for a self-contained deodorizing apparatus whereby the replaceable cartridge containing a quantity of deodorizing material, and the battery, are separately replaceable.

Yet another object of this invention is to facilitate ease of servicing and replacement of expendable components.

These and other objects are attained in accordance with the present invention wherein there is provided a self-contained battery-powered room deodorizer including a housing having an inlet portion through which ambient air is drawn into the housing by means of a battery powered fan. The air is passed about a quantity of vaporizable material contained within the housing, and then discharged therefrom into the ambient air carrying the vaporized portion of the product therewith. A replaceable deodorizing material containing cartridge is positionable within the housing, and provides a support well for supporting a replaceable battery, such that the deodorizing material and battery may be separately replaced when either of these items has become expended.

BRIEF DESCRIPTION OF THE DRAWINGS

Further objects of the invention together with additional features contributing thereto and advantages accruing therefrom will be apparent from the following description of a preferred embodiment of the invention which is shown in the accompanying drawings with like reference numerals indicating corresponding parts throughout, wherein:

FIG. 1 is a front planar view of an assembled self-contained deodorizing apparatus constructed in accordance with the invention;

FIG. 2 is a side elevation of the apparatus shown in FIG. 1 in an unassembled position, with portions removed, to better illustrate the construction thereof;

FIG. 3 is an enlarged, cross-sectional view of the apparatus shown in FIG. 1 taken along the lines 3—3;

FIG. 4 is a side planar view of the replaceable cartridge used in the air deodorizing apparatus;

FIG. 5 is a top planar view of the replaceable cartridge illustrated in FIG. 4;

FIG. 6 is a cross-sectional view of the cartridge shown in FIG. 4 taken along lines 6—6;

FIG. 7 is a bottom planar view of the cartridge shown in FIG. 4; and

FIG. 8 is a cross-sectional view of the apparatus shown in FIG. 4 taken along lines 8—8.

DESCRIPTION OF THE PREFERRED EMBODIMENT

Referring now to FIGS. 1-3, there is illustrated a self-contained air deodorizing device 100 which is formed in a substantially rectangular shape. The deodorizing device 100 comprises a two-part housing including a mounting section 10 adapted to secure the device to a vertical wall, and a closure section 50 which, when connected to the mounting section 10 together form a rectangular-shaped enclosure. The mounting section 10 includes a wall portion 11 having a pair of openings 12 formed therein by which the mounting section 10 may be secured to a vertical surface, or the mounting section can be attached to a wall by means of a pressure-sensitive adhesive-backed foam tape 13.

The uppermost end of the mounting section 10 is formed with a pair of vertically extending tabs 15, each of which is adapted to engage one of a pair of slots 55 formed in the upper end of the closure section 50 for securing the two sections together. The lowermost portion 16 of the mounting section 10 includes a plurality of slots 17 forming a discharge grille through which air is discharged from the deodorizing device. The forward edge 18 of the slot formation functions as a retainer to receive a tang 58 of a lip portion 57 of the closure section 50 for releasably securing the two housing sections 10 and 50 together.

The closure section 50 of the deodorizing device 100 is formed as a complementary portion for engaging the mounting section 10 to form the closure. To this end the closure section 50 has the pair of slots 55 formed in an upper closure wall 54 for engaging the tabs 15 of the mounting section 10. A plurality of slots 53 in the wall 54 from an inlet grille through which ambient air may be drawn into the deodorizer. A slidable slotted baffle plate 59 is carried by the wall 54 and is selectively movable into and out from interference with the slots 53 to control the quantity of air being passed through the deodorizer.

A pair of longitudinally extending tab portions 56 are formed, with one along each diagonal edge of the closure section 50, to engage a complementary diagonal undercut edge of the mounting section 10. Upon positioning the closure section with the tabs 15 adjacent to the slots 55, and lowering the closure section 50 into engagement with the mounting section 10, the tabs 15 of the mounting section will extend through the slots 55, and the tab portions 56 will be positioned within the side portions of the mounting section 10 forming the enclosure. As previously described, the lower end of the closure section 50 is formed with an outwardly extending lip 57 terminating with a tang 58 such that when the two sections of the housing are assembled, the tang 58 will be engaged with the forward edge 18 of the slot formation to assist in retaining and securing the two complementary sections together.

In order to generate the flow of ambient air through the deodorizer housing, a battery powered electric motor driven fan assembly 30 is positioned within the closure section 50 and supported between a pair of upper and lower guides 51 and 52, respectively, formed on each side wall 53' of the closure section. The guides 51 and 52 function to support the motor and fan assembly 30 adjacent to the air inlet slots 53 for drawing air into the unit. A two-piece bracket 31 is secured to the interior of a front wall 57' of the closure section and functions to complete a circuit, including a battery 32, when electrically coupled between the bracket and an electric battery-powered motor 33 of the motor and fan assembly. The motor 33 is preferably of a type which is operable in either a forward or a reverse direction of rotation depending upon the polarity coupling of the battery 32 in the bracket 31. In this manner the direction of rotation of a fan 34 can be changed, as desired, to reverse the direction of air flow through the enclosure to discharge the treated air out of either the slots 17 or 53.

As best illustrated in FIG. 3, the motor and fan assembly 30 includes the fan 34 encircled by a shroud 35, from which the electric motor 33 is supported, to direct air flow from the inlet 53 across a vaporizable material 37 contained within a disposable cartridge 40. The shroud 35 is preferably made of a transparent plastic material so that the operation of the fan 34 may be observed when inspecting the unit for servicing or after replacing the expendable materials. The replaceable cartridge 40, best shown in FIGS. 4–8, is circular in cross section, and has an open upper end 41 which conforms to a discharge opening 36 of the shroud 35. The upper end of cartridge 40 is also formed with a lip portion 42 to engage each of the lowermost guides 52 to support the cartridge 40 in a position adjacent to the discharge of air from the fan shroud 35.

The discharge end of the cartridge 40 is tapered, and includes a plurality of openings 43 for permitting free flow of air over and about the vaporizable material 37 contained therein. A well 45, formed by a concentric inner wall 46, is formed in the cartridge and in cooperation with a base ring 47 of the cartridge bottom forms a battery chamber for supporting and positioning the battery 32 concentrically within the cartridge 40. The well or battery chamber 45 is sized to permit easy insertion and removal of the battery 32 from the chamber for replacement when necessary. The space between the outer surface of the inner wall 46 and the inner surface of an outer wall 48 of the cartridge 40 is used to hold the quantity of vaporizable material 37, and properly position this material in the air stream emitted by the fan 34. To this end, the inner face of the outer wall 48 of the cartridge includes a plurality of circumferentially spaced rib portions 49 which retain this material and ensure its proper position in the air flow. These rib portions 49 extend vertically upward at the joinder of the outer wall 48 and the base ring 47 to position the free end of inner wall 46.

In operation, a cartridge 40 containing deodorizing material 37 has a battery 32 inserted in the battery chamber 45, and the cartridge and battery are inserted into the closure section 50. The lower or tapered portion of the cartridge 40 engages the lowermost portion of the bracket 31 which functions to electrically couple one of the terminals of the battery 32 in an electrical circuit for energizing the fan motor 33. Upon insertion of the upper portion of the cartridge into the guides 52, the opposite terminal for the battery 32 will be engaged by the other portion of bracket 31 which electrically couples the battery for completing the circuit to energize the motor 33 and initiate air movement. The fan motor 33 will then run until such time as it is necessary to replace the battery power source. However, when replacing a discharged battery 32, if it is found that deodorizing material 37 is still contained within the cartridge 40, the battery 32 may be replaced by merely removing the cartridge 40 and inserting a fresh battery in place of the one that has been discharged. In this manner, the entire cartridge 40 does not need to be replaced merely because the battery 32 has been discharged. Similarly, if it is found that the vaporizable material 37 has been expended, the battery may merely be removed from the cartridge 40 containing the expended material 37, and the battery 32 inserted into a new cartridge 40 containing fresh material.

While the invention has been described in the specification and illustrated in the drawings with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment illustrated by the drawings and described in the specification as the best mode presently contemplated for carrying out this invention, but that the invention will include any embodiments falling within the description of the appended claims.

We claim:

1. A disposable air freshening or deodorizing cartridge for use in supporting a battery within a self-contained air freshener appartus comprising [a cylindrical]

*an* outer wall and a battery positioning [cylindrical] inner wall [positioned concentric] within said outer wall *defining a battery receiving compartment*,

[first] spacer means extending transversely between and connected to a first end of said outer wall and a first end of said inner wall for [concentrically] spacing said inner and outer walls one from the other forming an opening for an air passageway therebetween, said battery positioning [cylindrical] inner wall extending a length greater than said [cylindrical] outer wall, a battery support [ring] carried by a second end of said outer wall and positioned transverse to a second free end of said battery positioning inner wall, said battery support [ring] extending a width sufficient to form at least a partial closure of said *battery receiving compartment at said second* free end of said battery positioning inner wall *and cooperating with said inner wall for supporting and positioning a battery within the cartridge*, and connecting means extending between said second end of said outer wall and said *battery* support [ring], forming a tapered end of the cartridge [and an opening for] *which defines a plurality of openings permitting free flow of air through* said air passageway between said inner and outer walls.

2. The disposable air freshening cartridge of claim 1 further including a quantity of vaporizable deodorizing material carried within said cartridge between an inner surface of said outer wall and an outer surface of said inner wall in said air passageway formed between said walls.

3. [The disposable air freshening cartridge of claim 2 further including] *A disposable air freshening or deodorizing cartridge for use in supporting a battery within a self-contained air freshener apparatus comprising an outer wall and a battery positioning inner wall within said outer wall, spacer means extending transversely between and connected to said outer wall and said inner wall for spacing said inner and outer walls one from the other forming an opening for an air passageway therebetween, said battery positioning inner wall extending a length greater than said outer wall, a battery support carried by said outer wall and positioned transverse to said battery positioning inner wall, said battery support extending a width sufficient to form at least a partial closure of said battery positioning inner wall, and connecting means extending between said outer wall and said support forming a tapered end of the cartridge and an opening for said air passageway between said inner and outer walls, a quantity of vaporizable deodorizing material carried within said cartridge between an inner surface of said outer wall and an outer surface of said inner wall in said air passageway formed between said walls, and* a plurality of positioning ribs [circumferentially] spaced about the inner surface of said outer wall and extending inwardly toward the outer surface of said inner wall for positioning said quantity of vaporizable deodorizing material carried in said air passageway formed between said inner and outer walls.

4. The disposable air freshening cartridge of claim 3 wherein said plurality of positioning ribs extend outwardly from the joinder of said connecting means and said battery support [ring] adjacent to the outer surface of said inner wall for positioning [said free end of] said inner wall relative to said battery support [ring].

5. The disposable air freshening cartridge of claim 2 further including a battery removably positioned within said battery positioning inner wall and carried by said battery support [ring].

6. In a self-contained air freshening or deodorizing apparatus wherein a quantity of a product capable of being vaporized to release the product in vapor form is contained within a disposable cartridge positionable within the apparatus in a flow of air movement generated by a battery powered air movement device, the improvement comprising a disposable air freshening or deodorizing cartridge having [a cartridge] *an* outer wall and a battery positioning [cylindrical] inner wall [positioned concentric] within said outer wall *defining a battery receiving compartment*,

[first] spacer means extending transversely between and connected to a first end of said outer wall and a first end of said inner wall for [concentrically] spacing said inner and outer walls one from the other forming an inlet for an air passageway therebetween, said battery positioning [cylindrical] inner wall extending a length greater than said [cylindrical] outer wall, a battery support [ring] carried by a second end of said outer wall and positioned transverse to a second free end of said battery positioning inner wall, said battery support [ring] extending a width sufficient to form at least a partial closure of said *battery receiving compartment at said second* free end of said battery positioning inner wall *and cooperating with said inner wall for supporting and positioning a battery within the cartridge*, and connecting means extending between said second end of said outer wall and said *battery* support [ring], forming a tapered end of the cartridge [and an outlet for] *which defines a plurality of openings permitting free flow of air through* said air passageway between said inner and outer walls.

7. The self-contained air freshening or deodorizing apparatus of claim 6 wherein said disposable air freshening cartridge further includes a quantity of vaporizable deodorizing material carried within said cartridge between an inner surface of said outer wall and an outer surface of said inner wall in said air passageway formed between said walls.

8. [The self-contained air freshening or deodorizing apparatus of claim 6 wherein said disposable air freshening cartridge further includes] *In a self-contained air freshening or deodorizing apparatus wherein a quantity of a product capable of being vaporized to release the product in vapor form is contained within a disposable cartridge positionable within the apparatus in a flow of air movement generated by a battery powered air movement device, the improvement comprising*

*a disposable air freshening or deodorizing cartridge having an outer wall and a battery positioning inner wall within said outer wall,*

*spacer means extending transversely between and connected to said outer wall and said inner wall for spacing said inner and outer walls one from the other forming an inlet for an air passageway therebetween,*

*said battery positioning inner wall extending a length greater than said outer wall,*

*a battery support carried by said outer wall and positioned transverse to said battery positioning inner wall,*

*said battery support extending a width sufficient to form at least a partial closure of said battery positioning inner wall, and*

*connecting means extending between said outer wall and said support forming a tapered end of the cartridge and an outlet for said air passageway between said inner and outer walls, a quantity of vaporizable deodorizing material carried within said cartridge between an inner surface of said outer wall and an outer surface of said inner wall in said air passageway formed between said walls, and* a plurality of positioning ribs [circumferentially] spaced about the inner surface of said outer wall and extending inwardly toward the outer surface of said inner wall for positioning said quantity of vaporizable deodorizing material carried in said air passageway formed between said inner and outer walls.

9. The self-contained air freshening or deodorizing apparatus of claim 8 wherein said plurality of positioning ribs of said disposable air freshening cartridge extend outwardly from the joinder of said connecting means and said battery support [ring] adjacent to the outer surface of said inner wall for positioning [said free end of] said inner wall relative to said battery support [ring].

10. The self-contained air freshening or deodorizing apparatus of claim 7 wherein said disposable air freshening cartridge further includes a battery removably positioned within said battery positioning inner wall and carried by said battery support [ring].

11. A self-contained air freshening or deodorizing apparatus comprising a two-part housing including a mounting section for securing the apparatus in an operative position and a closure section for connection to said mounting section for forming an enclosure, mounting means operatively connected to said mounting section for fastening said mounting section to a supporting surface, said mounting section including releasable coupling means engageable with said closure section to releasably connect said mounting section and said closure section forming an enclosure, battery-powered air movement generating means supported within said closure section for generating a path of air flow through said enclosure, and air freshening or deodorizing means for supplying a source of vaporizable material to said path of air flow, said air freshening or deodorizing means being carried within said closure section such that said battery-powered air movement generating means and said air freshening or deodorizing means are removable from said mounting section with said closure section to facilitate servicing.

12. The self-contained air freshening or deodorizing apparatus of claim 11 wherein said air freshening or deodorizing menas comprises a replaceable cartridge.

13. The self-contained air freshening or deodorizing apparatus of claim 12 wherein said air freshening or deodorizing means includes

[a cylindrical] *an* outer wall and a battery positioning [cylindrical] inner wall [positioned concentric] within said outer wall,

[first] spacer means extending transversely between and connected to [a first end of] said outer wall and [a first end of] said inner wall for [concentrically] spacing said inner and outer walls one from the other forming an inlet for an air passageway therebetween, said battery positioning [cylindrical] inner wall extending a length greater than said [cylindrical] outer wall, a battery support [ring] carried by [a second end of] said outer wall and positioned transverse to [a second free end of] said battery positioning inner wall, said battery support [ring] extending a width sufficient to form at least a partial closure [of said free end] of said battery positioning inner wall, and connecting means extending between [said second end of] said outer wall and said support [ring] forming a tapered end of the cartridge and an outlet for said air passageway between said inner and outer walls.

14. The self-contained air freshening or deodorizing apparatus of claim 13 wherein said disposable air freshening cartridge includes a quantity of vaporizable deodorizing material carried within said cartridge between an inner surface of said outer wall and an outer surface of said inner wall in said air passageway formed between said walls.

15. The self-contained air freshening or deodorizing apparatus of claim 14 wherein said disposable air freshening cartridge further includes a plurality of positioning ribs [circumferentially] spaced about the inner surface of said outer wall and extending inwardly toward the outer surface of said inner wall for positioning said quantity of vaporizable deodorizing material carried in said air passageway formed between said inner and outer walls.

16. The self-contained air freshening or deodorizing apparatus of claim 15 wherein said plurality of positioning ribs of said disposable air freshening cartridge extend outwardly from the joinder of said connecting means and said battery support [ring] adjacent to the outer surface of said inner wall for positioning [said free end of] said inner wall relative to said battery support [ring].

17. The self-contained air freshening or deodorizing apparatus of claim 14 wherein said disposable air freshening cartridge further includes a battery removably positioned within said battery positioning inner wall and carried by said battery support [ring].

18. The self-contained air freshening or deodorizing apparatus of claim 12 further including guide means carried by said closure section for positioning said replaceable air freshening or deodorizing cartridge adjacent to said battery-powered air movement generating means.

19. The self-contained air freshening or deodorizing apparatus of claim 11 further including air flow restricting means carried by said closure section in said path of air flow for selectively changing the quantity of air passing through said enclosure.

20. The self-contained air freshening or deodorizing apparatus of claim 11 wherein said closure section includes tab means extending outwardly therefrom for engagement with said mounting section to releasably couple said closure section to said mounting section for forming an enclosure.

21. The self-contained air freshening or deodorizing apparatus of claim 11 further including a shroud surrounding said battery-powered air movement generating means supported within said enclosure for controlling the air flow generated by said air movement generating means.

22. The self-contained air freshening or deodorizing apparatus of claim 21 wherein said shroud includes a transparent portion such that operation of said battery-powered air movement generating means is observable through said transparent portion.

23. The self-contained air freshening or deodorizing apparatus of claim 11 wherein said battery-powered air movement generating means generates a path of air flow through said enclosure in a direction determined by the polarity coupling of a battery coupled thereto.

*24. A disposable air freshening or deodorizing cartridge for use in supporting a battery within a self-contained air freshener apparatus comprising an outer wall and a battery positioning inner wall within said outer wall defining a battery receiving compartment,*

*spacer means extending transversely between a first end of said outer wall and a first end of said inner wall spacing said inner and outer walls one from the other forming an opening for an air passageway therebetween,*

*a battery support carried by said outer wall and positioned transverse to said battery positioning inner wall near a second end of said inner wall,*

*said battery support extending a width sufficient to form at least a partial closure of said battery receiving compartment near one end of said battery positioning inner wall and cooperating with said inner wall for supporting and positioning a battery within the cartridge, and*

*connecting means extending between a second end of said outer wall and said battery support, forming an opening for said air passageway between said inner and outer walls.*

*25. The disposable air freshening cartridge of claim 24 further including a quantity of vaporizable deodorizing material carried within said cartridge between an inner surface of said outer wall and an outer surface of said inner wall in said air passageway formed between said walls.*

*26. The disposable air freshening cartridge of claim 24 further including a battery removably positioned within said battery positioning inner wall and supported by said battery support.*

*27. In a self-contained air freshening or deodorizing apparatus wherein a quantity of a product capable of being vaporized to release the product in vapor form is contained within a disposable cartridge positionable within the apparatus in a flow of air movement generated by a battery powered air movement device, the improvement comprising*

*a disposable air freshening or deodorizing cartridge having an outer wall and a battery positioning inner wall within said outer wall defining a battery receiving compartment,*

*spacer means extending transversely between and connected to a first end of said outer wall and a first end of said inner wall for spacing said inner and outer walls one from the other forming an inlet for an air passageway therebetween,*

*a battery support carried by said outer wall and positioned transverse to said battery positioning inner wall near a second end of said inner wall,*

*said battery support extending a width sufficient to form at least a partial closure of said battery receiving compartment near one end of said battery positioning inner wall and cooperating with said inner wall for supporting and positioning a battery within the cartridge, and*

*connecting means extending between a second end of said outer wall and said battery support, forming an outlet for said air passageway between said inner and outer walls.*

*28. The self-contained air freshening or deodorizing apparatus of claim 27 wherein said disposable air freshening cartridge further includes a quantity of vaporizable deodorizing material carried within said cartridge between an inner surface of said outer wall and an outer surface of said inner wall in said air passageway formed between said walls.*

*29. The self-contained air freshening or deodorizing apparatus of claim 28 wherein said disposable air freshening cartridge further includes a battery removably positioned within said battery positioning inner wall and carried by said battery support.*

*30. A self-contained air freshening or deodorizing apparatus comprising*

*a two-part housing including a mounting section adapted for fastening to a supporting surface and a closure section for connection to said mounting section for forming an enclosure,*

*said mounting section including releasable coupling means engageable with said closure section to releasably connect said mounting section and said closure section forming said enclosure,*

*battery-powered air movement generating means, said closure means including support means supporting said air movement generating means within said closure section for generating a path of air flow through said enclosure, and*

*air freshening or deodorizing means in said enclosure for supplying a source of vaporizable material to said path of air flow,*

*said battery-powered air movement generating means being removable from said mounting section with said closure section to facilitate servicing.*

*31. The self-contained air freshening or deodorizing apparatus of claim 30 wherein said disposable air freshening means includes a cartridge having a quantity of vaporizable deodorizing material carried therewithin.*

*32. The self-contained air freshening or deodorizing apparatus of claim 31 wherein said cartridge further includes a battery removably positioned therewithin.*

*33. The self-contained air freshening or deodorizing apparatus of claim 30 wherein said mounting section has an upstanding rear wall and first and second side walls each having an upper edge portion, and wherein said closure section has an upper closure wall, a front wall and first and second side walls, each of said closure section side walls having longitudinally extending undercut edge portions adapted to mate with said upper edge portions of said mounting section side walls and said closure section being slidable vertically relative to said mounting section for removal therefrom.*

*34. The self-contained air freshening or deodorizing apparatus of claim 33 wherein the uppermost end of said mounting section has at least one vertically extending tab, and wherein said upper closure wall has at least one slot for engaging said tab for securing said two sections together.*

*35. A self-contained air freshening or deodorizing apparatus comprising*

*a two-part housing including a mounting section securing the apparatus in an operative position and a closure section for connection to said mounting section for forming an enclosure,*

*mounting means operatively connected to said mounting section for fastening said mounting section to a support surface,*

*said mounting section including releasable coupling means engageable with said closure section to releasably connect said mounting section and said closure section forming said enclosure,*

*battery-powered air movement generating means supported within said closure section for generating a path of air flow through said enclosure, and*

*air freshening or deodorizing means in said enclosure for supplying a source of vaporizable material to said path of air flow,*

*said battery-powered air movement generating means being removable from said mounting section with said closure section to facilitate servicing.*

*36. The self-contained air freshening or deodorizing apparatus of claim 35 wherein said air freshening or deodorizing means comprises a replaceable cartridge.*

*37. The self-contained air freshening or deodorizing apparatus of claim 35 wherein said mounting section has an upstanding rear wall and first and second side walls each having an upper edge portion, and wherein said closure section has an upper closure wall, a front wall and first and second side walls, each of said closure section side walls having longitudinally extending undercut edge portions adapted to mate with said upper edge portions of said mounting section side walls and said closure section being slidable vertically relative to said mounting section for removal therefrom.*

*38. The self-contained air freshening or deodorizing apparatus of claim 37 wherein the uppermost end of said mounting section has at least one vertically extending tab, and wherein said upper closure wall has at least one slot for engaging said tab for securing said two sections together.*

* * * * *

UNITED STATES PATENT AND TRADEMARK OFFICE

CERTIFICATE OF CORRECTION

PATENT NO. : Re. 33,864

DATED : March 31, 1992

INVENTOR(S) : Robert L. Steiner and Thomas R. Bajek

It is certified that error appears in the above-identified patent and that said Letters Patent is hereby corrected as shown below:

Col. 6, line 50, [a cartridge] should be --[a cylindrical]--.

Col. 9, line 41, before "21", insert --[19]--.

Signed and Sealed this

Fifteenth Day of June, 1993

Michael K. Kirk

MICHAEL K. KIRK

*Acting Commissioner of Patents and Trademarks*

*Attest:*

*Attesting Officer*